(12) United States Patent
Abramov et al.

(10) Patent No.: US 11,534,469 B2
(45) Date of Patent: Dec. 27, 2022

(54) METHOD FOR THE STIMULATION OF HUMAN IMMUNE CELLS

(71) Applicant: Vita Motus AG, Wattwil (CH)

(72) Inventors: Aleksandr Abramov, Moscow (RU); Alisa Petkevic, Moscow (RU); Vadim Pospelov, Ullisbach (CH)

(73) Assignee: Vita Motus AG, Wattwil (CH)

( * ) Notice: Subject to any disclaimer, the term of this patent is extended or adjusted under 35 U.S.C. 154(b) by 81 days.

(21) Appl. No.: 17/002,169

(22) Filed: Aug. 25, 2020

(65) Prior Publication Data

US 2022/0062358 A1   Mar. 3, 2022

(51) Int. Cl.
*A61K 36/02* (2006.01)
*A61K 9/00* (2006.01)

(52) U.S. Cl.
CPC ............ *A61K 36/02* (2013.01); *A61K 9/0053* (2013.01)

(58) Field of Classification Search
None
See application file for complete search history.

(56) References Cited

U.S. PATENT DOCUMENTS

2012/0302742 A1* 11/2012 Hjelland ............. C08B 37/0003
  536/122
2012/0315261 A1* 12/2012 Shin ....................... A23L 3/3472
  424/195.17
2018/0289759 A1* 10/2018 Campos .................. A61P 31/04

FOREIGN PATENT DOCUMENTS

RU    2498821 C1    11/2013
RU    2717672 C1     3/2020

* cited by examiner

*Primary Examiner* — Michael Barker
*Assistant Examiner* — Randall O Winston
(74) *Attorney, Agent, or Firm* — The Webb Law Firm

(57) ABSTRACT

Provided herein is a substance for use in a therapeutic method for stimulating cells in the human immune system, a method for producing this substance, and a method of use of the substance for stimulating cells of the human immune system in treating various diseases involving immune system disorders.

2 Claims, No Drawings

METHOD FOR THE STIMULATION OF HUMAN IMMUNE CELLS

BACKGROUND OF THE INVENTION

Technical Field

The invention pertains to the domain of medicine, particularly immunology, and can be used for stimulating cells of the human immune system in treating various diseases involving immune system disorders.

Description of Related Art

A known immunopotentiation method uses Panagen (No. LSR-004429/08), administered in the form of tablets or intramuscular solution, that stimulates endogenous production of cytokines and hematopoietic factors (patent: RU 2498821 C1, published on 4 Oct. 2012). The drug is double-stranded fragmented human genomic DNA with fragments 200 to 6000 base pairs long. This method fails to achieve highly efficient immunopotentiation due to the medicine's low bioavailability, and losses during passage through segments of the digestive system if taken orally. On the other hand, like any foreign DNA, it may be actively destroyed; also, being a specific nucleotide sequence, it may induce negative responses by interfering with DNA structure in human cells.

Panagen is used in tableted form, three tablets per day, containing 5 mg of the active substance, for one to fourteen days since the start of administration or until therapeutic benefit is achieved. If used in tableted form, the foreign DNA-based medicine may lose much of its active substance and efficiency.

SUMMARY

Our proposed method aims to create a medication for stimulating human immune cells that is devoid of the known drug's deficiencies, with higher bioavailability and cell penetration capability due to both its active substances' small size (5-10 kD) and smaller losses during passage through the digestive system on account of the chemical structure of its active components that mainly include polysaccharides.

To work around that problem, we obtain a human immune cell stimulant by leaching homogenate of *Laminaria japonica* and *Laminaria angustata* algae with aqueous and isobutanolic solution, with 1 g:2.5 ml:2.5 ml mix ratio, to obtain a homogeneous mixture which is then cured at 60° C. for one hour and incubated for 10-15 hours at room temperature; then supernatant fluid is withdrawn and centrifuged at 3000 rpm and +4° C. for 30 minutes. The centrifuged supernatant is placed into a vacuum evaporator and blown through with argon, then vacuum-dried for one hour at room temperature and then at 60° C. until all liquid fraction evaporates. The resultant sediment is diluted with water into 5% solution and then ultracentrifuged at 100,000 rpm for one hour; the resulting supernatant is withdrawn and centrifuged in 10 kD filter tubes for one hour at 5000 rpm, after which the lower percolated fraction is withdrawn and centrifuged in 5 kD filter tubes for one hour at 5000 rpm. Now the upper fraction detained by the filter is withdrawn and diluted in 500 ml of NaCl saline for a final concentration of 10 mg/ml.

In a further embodiment, after centrifugation at 3000 rpm and +4° C. for 30 minutes and before the centrifuged supernatant is placed into a vacuum evaporator and purged with argon, the centrifuged supernatant is ultracentrifuged at 100,000 rpm for one hour.

A second aspect of the invention comprises the substance produced by the method described above.

A further aspect of the invention comprises the substance, which is produced by the method described above, for use in a therapeutic method for stimulating cells in the human immune system. In a preferred embodiment, this substance is administered orally, preferably in 1 ml dosage once daily, for example before meals, for a fortnight.

DETAILED DESCRIPTION

Enterocytes and goblet cells, found in extrathoracic trachea and pancreatic and parotid ducts as well as segments of the digestive system, are three times more permeable to 5-10 kD molecules than other digestive system cells, including stem and Paneth cells. Consequently, the cell pools partly responsible for tissue immunity manifestations and the digestive system's protective functions and also for the ingress of substances from the digestive system into the bloodstream turn out to be the cell pools most permeable to the algal extract as compared to others. As a result, the active algal extract can enter the bloodstream both paracellularly and transcellularly (through the enterocytes). The greater permeability of certain digestive system cells and the algal extract's small particle size (5-10 kD) and lack of a complicated 3D structure combine to make it highly bioavailable. Studies of the medication's efficiency showed 1 ml once-daily ante cibum oral administration to be the safest and most efficient regimen.

The above method for obtaining individual fractions of *Laminaria japonica* and/or *Laminaria angustata* consisting of 5 to 10 kD molecules seems optimal and permits more than 10,000-fold enrichment of the fraction from its initial content.

The proposed method's algorithm is as follows:

To obtain the said fractions from dried and powdered homogenate of algae (*Laminaria japonica* and *Laminaria angustata*) by leaching with butanol and water mixture, we leach powdered *Laminaria* in water and isobutanol solution (1 g:2.5 ml:2.5 ml). To this end, we pour 500 ml of isobutanol into a 12 l bottle, then add 200 g of powdered *Laminaria* and stir until the solution is homogeneous and dark green in colour. Ten minutes later, we add 500 ml of distilled water into the bottle and stir again until homogeneous. The resultant mixture is heated in water bath or a thermostat at 60° C. and then incubated for 10-15 hours at room temperature; then supernatant is withdrawn and centrifuged in an Eppendorf Centrifuge 5804 R at 3000 rpm and +4° C. for 30 minutes. The supernatant thus obtained should be withdrawn, placed into a vacuum evaporator and blown through with argon. The resultant supernatant is then vacuum-dried as follows: at room temperature for one hour, to avoid ebullition as suction is applied, and then at 60° C. until complete evaporation. Then we prepare 5% aqueous solution and ultracentrifuge it at 100,000 rpm for one hour. The resulting supernatant should be withdrawn and centrifuged again, now in 10 kD filter tubes, for one hour at 5000 rpm on the Eppendorf Centrifuge 5804 R apparatus. The lower percolated fraction is then withdrawn and centrifuged in 5 kD filter tubes, for one hour at 5000 rpm on the Eppendorf Centrifuge 5804 R7 apparatus. Then the upper fraction detained by the filter is withdrawn and 500 ml of NaCl saline is added. The medication obtained is used as follows: 1 ml of the medication is diluted in 20 ml of water and ingested once a day before a meal for two weeks. The medication consists of 5 to 10 kD molecules.

Example 1

A female patient, aged 40, was referred to an immunologist by her GP as she had had frequent ARD episodes (4-5 per year) in the past three years and complained of fatigue, drowsiness and persistent weakness. Her history was unburdened, with two pregnancies, both delivered (at the age of 23 and 27); physical examination found no abnormalities. The blood cell count and chemistry tests and clinical urine test found none, either. The immunologist ordered an examination of her immune status, which found a reduced pool of natural killers and B lymphocytes while their absolute values remained normal. The patient was started on our medication, with 1 ml administered orally in 20 ml of water before meals, once daily for two weeks. One month after the start of treatment, the patient noted a subjective improvement in her status, with lesser weakness and fatigue; she found it easier to get up in the morning (while her daily regimen remained the same). Objectively, re-examination of her immune status showed an increase in her natural killer and B lymphocyte pools that doubled and trebled, respectively.

| Indicator | Value found, % | | Norm | |
|---|---|---|---|---|
| | Before the course | One month after | % (for cells) | Absolute |
| T lymphocytes (CD3+) | 68 | 66 | 66-76 | $1.4\text{-}2*10^9$ |
| B lymphocytes (CD19+) | 5 | 10 | 12-22 | $0.3\text{-}0.5*10^9$ |
| T helpers (CD3+ CD4+) | 39 | 35 | 33-41 | $0.7\text{-}1.1*10^9$ |
| Cytotoxic T cells (CD3+, CD8+) | 29 | 33 | 27-35 | $0.6\text{-}0.9*10^9$ |
| Natural killers (CD3+, CD16+, CD56+) | 2 | 6 | 4-27 | $0.1\text{-}0.5*10^9$ |
| CD4/CD8 | 1.3 | 1.3 | 1-1.5 | |
| Ig A, mg/ml | 2.0 | 2.5 | 1.03-4.61 | |

Example 2

A male patient aged 60, with no abnormal history, consulted the immunologist on his own and reported occasional joint pains, acrimony and sleeping problems (difficulty falling asleep and awakening). Examination at the internal medicine department of a private clinic found no abnormalities. Immune status examination showed decreased count of natural killers (relatively) and humoral immunity factors (IgA and IgM). The patient was started on our medication, with 1 ml administered orally in 20 ml of water before meals, once daily for two weeks. One month after start of treatment, the patient reported better sleep (quick going to sleep with no waking in the night) and improved mood. Noted objectively one month after the start of treatment were an increase in humoral immunity factors and normalized lymphocyte population ratios.

| Indicator | Value found, % | | Norm | |
|---|---|---|---|---|
| | Before the course | One month after | % (for cells) | Absolute |
| T lymphocytes (CD3+) | 75 | 76 | 66-76 | $1.4\text{-}2*10^9$ |
| B lymphocytes (CD19+) | 15 | 17 | 12-22 | $0.3\text{-}0.5*10^9$ |
| T helpers (CD3+ CD4+) | 32 | 32 | 33-41 | $0.7\text{-}1.1*10^9$ |
| Cytotoxic T cells (CD3+, CD8+) | 31 | 29 | 27-35 | $0.6\text{-}0.9*10^9$ |
| Natural killers (CD3+, CD16+, CD56+) | 3.5 | 10 | 4-27 | $0.1\text{-}0.5*10^9$ |
| CD4/CD8 | 1.3 | 1.3 | 1-1.5 | |
| Ig A, mg/ml | 0.5 | 2.7 | 1.03-4.61 | |
| Ig G, mg/ml | 7.5 | 8 | 6.2-14.7 | |
| Ig M, mg/ml | 0.3 | 0.51 | 0.61-1.64 | |

The above examples show that the medication whose active substance is 5-10 kD molecules from *Laminaria japonica* and *Laminaria angustata* leads to normalization of the patients' immune status and a subjective feeling of improved health.

The invention claimed is:

1. A method for producing a substance, the method comprising:
   leaching homogenate of *Laminaria Japonica* and *Laminaria* Angustata algae with a mixture of an aqueous solution and an isobutanolic solution, with a 1 g:2.5 ml:2.5 ml mix ratio, to obtain a homogeneous mixture;
   heating the homogenous mixture at 60° C. for one hour;
   incubating the homogenous mixture for 10-15 hours at room temperature to obtain a supernatant;
   withdrawing the supernatant from the homogenous mixture and centrifuging the supernatant at 3000 rpm and +4° C. for 30 minutes to obtain a centrifuged supernatant;
   purging the centrifuged supernatant with argon to obtain a purged, centrifuged supernatant and vacuum drying the purged, centrifuged supernatant for one hour at room temperature, followed by vacuum drying at 60° C. until a liquid fraction of the supernatant evaporates, to obtain a sediment;
   diluting the sediment with water to produce a 5% solution and then ultracentrifuging the 5% solution at 100,000 rpm for one hour to obtain a second supernatant;
   withdrawing the second supernatant and centrifuging the second supernatant in 10 kD filter tubes for one hour at 5000 rpm to obtain a lower percolated fraction;
   withdrawing the lower percolated fraction and centrifuging the lower percolated fraction in 5 kD filter tubes for one hour at 5000 rpm to obtain an upper fraction detained by a filter in the filter tubes; and
   withdrawing the upper fraction from the filter and diluting the upper fraction in 500 ml of NaCl saline to obtain a substance with a final concentration of 10 mg/ml.

2. The method according to claim 1, further comprising, after centrifuging the supernatant and prior to purging the centrifuged supernatant, ultracentrifuging the centrifuged supernatant at 100,000 rpm for one hour.

* * * * *